United States Patent [19]

Molozay et al.

[11] Patent Number: 5,305,630
[45] Date of Patent: Apr. 26, 1994

[54] PROCESS AND APPARATUS FOR SUPPLYING GAS TO A VERY HIGHLY SENSITIVE ANALYZER

[75] Inventors: Maurice Molozay, Le Mesnil Saint Denis; Gérard Loiseau, Bois D'Arcy; Catherine Bonge, Paris, all of France

[73] Assignee: l'Air Liquid, Societe Anonyme pour l'Etude et l'Exploitation des Procedes Georges Claude, Paris, France

[21] Appl. No.: 760,977

[22] Filed: Sep. 17, 1991

[30] Foreign Application Priority Data

Oct. 2, 1990 [FR] France ................. 90 12101

[51] Int. Cl.⁵ ............................ G01D 18/00
[52] U.S. Cl. ........................ 73/1 G; 73/31.03
[58] Field of Search .......... 73/1 G, 23.21, 31.02, 73/31.03, 864.81, 864.85; 436/8, 9, 11, 18

[56] References Cited

U.S. PATENT DOCUMENTS

| | | | |
|---|---|---|---|
| 3,776,023 | 12/1973 | Budd et al. | 73/1 G |
| 4,063,446 | 12/1977 | Fuhrmann | 73/1 G |
| 4,436,699 | 3/1984 | Narato et al. | 340/647 X |
| 4,588,422 | 5/1980 | Raimond | 73/864,81 X |
| 4,656,865 | 4/1987 | Callan | 73/38 |
| 5,157,957 | 10/1992 | Metles et al. | 73/1 G |
| 5,214,952 | 6/1993 | Leggett et al. | 73/1 G |

FOREIGN PATENT DOCUMENTS

| | | |
|---|---|---|
| 0370151 | 5/1990 | European Pat. Off. |
| 0370871 | 5/1990 | European Pat. Off. |
| 2093653 | 1/1972 | France |
| 173740 | 10/1982 | Japan ................. 73/1 G |
| 1385067 | 3/1988 | U.S.S.R. ............. 73/1 G |

*Primary Examiner*—Tom Noland
*Attorney, Agent, or Firm*—Young & Thompson

[57] ABSTRACT

The line of gas to be analyzed, the "zero" gas line and calibration gas line are each provided with a restriction operating in sonic rate supplying a nominal constant flow and downstream, have a discharge duct provided with a flow regulator. The nominal flows in the first and second lines are higher than the given flow supplied to the analyzer so that during each of the calibration and analysis steps, the whole of the circuit portion of the device is permanently flushed with the nominal gas of the line and/or by a portion of the recirculated flow of gas originating from another line.

10 Claims, 2 Drawing Sheets

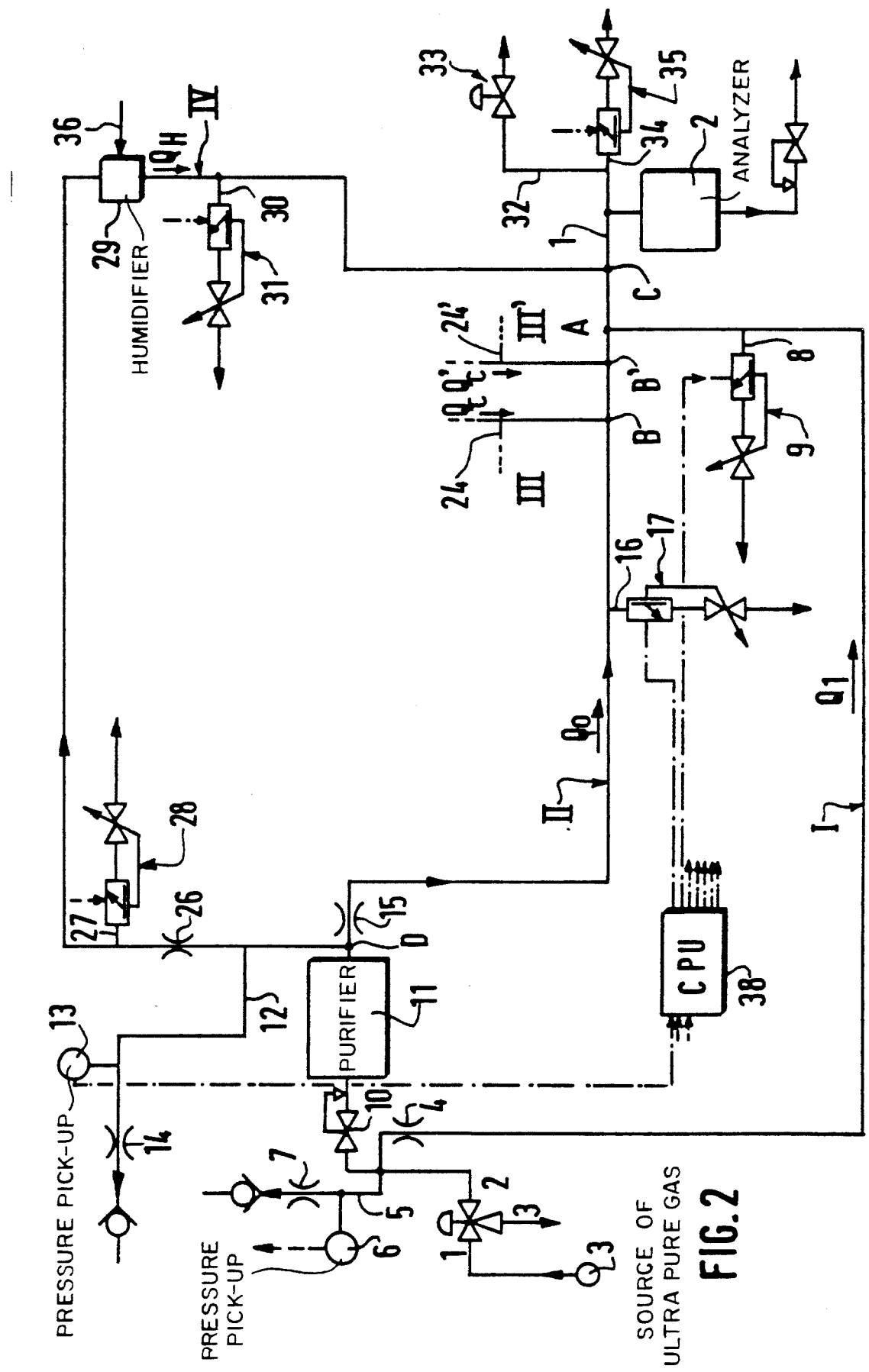

PROCESS AND APPARATUS FOR SUPPLYING GAS TO A VERY HIGHLY SENSITIVE ANALYZER

BACKGROUND OF INVENTION (a) Field of the Invention

The present invention concerns the processes for supplying gas to a very sensitive analyzer, for detecting traces of residual gases in a pure gas (herein after called "traces"), of the type comprising the sequential steps of supplying to a section of an input line to the analyzer, a given flow:

a) of a gas to be analyzed, via a first line,
b) of a pure gas prepared by purifying the gas to be analyzed, via a second line,
c) at least one calibration gas, which is diluted with the pure gas, and which initially contains larger traces of residual gases than the gas to be analyzed, via a third line, the downstream section of the three lines all meeting the section of the input line.

(b) Description of Prior Art

The utilization of very sensitive analyzers for detecting traces of impurities, such as of the ultrasensitive hygrometer or Fourier transformed infrared spectroscope (FTIR) type, which are capable of detecting and analyzing traces of gases at levels lower than ppb and which are used for example for very high purity gases (nitrogen, argon) in the very highly integrated semiconductor industry (VLSI), requires being able to sequentially supply to the analyzer, at a given flow, the gas to be analyzed, a so-called "zero" gas, obtained by purification of the gas to be analyzed and qualifying the zero of the analyzer, and a calibration gas, obtained by a high dilution of a gas initially containing a given and important quantity of traces, so as to calibrate the reading range of the analyzer.

The known processes and devices utilize three lines each provided with a flow regulator and a stop valve to isolate the lines which are of no interest in one of the steps for supplying gas to the analyzer. These processes have two major disadvantages because the flow regulators constitute polluting components which are susceptible to add uncontrolled traces or impurities to the various lines of gas, and during the periods where the lines are isolated, the gas present therein is susceptible to be rapidly polluted by mere absorption or desorption through the walls of the tubes.

To substantially reduce the above disadvantages, a process and a device have been proposed where each line is provided with a loss of static charge, which is less polluting than a flow regulator, and where, in the downstream section of the line, a three-way valve enables the isolation and flushing of the upstream section of the line. This approach enables reducing the tube lengths which are isolated and have not been flushed but does not completely remove these lengths. On the other hand, the feeding pressure into the first and second lines may vary within a wide range, so that the proposed process and device present the risks of an important time lag not permitting assuring the supply of a given flow to the analyzer, and consequently, possibly falsifying the precision of the measurements.

SUMMARY OF THE INVENTION

It is an object of the present invention to propose a process for supplying gas to an analyzer enabling preventing the presence of any polluting component along the path of the various gases by maintaining all the lines of the system under permanent flushing, to ensure that the regulation of the flow is exact and not very susceptible to time lag, and consequently to guarantee a reliable and substantially improved quality of analysis.

For this purpose, according to a characteristic of the invention, the gas permanently runs at a constant flow through the upstream parts of each of the three lines, there is provided in an intermediate part of each line, a discharge by-pass provided with a controllable flow regulator, the constant flow in the first and second lines being higher than the given flow for the analyzer, and for each of the steps a) and b) above-mentioned, the flow regulators are controlled so that a first part of the excess gas flow in the line corresponding to a step is withdrawn through the associated by-pass and second and third parts of the excess flow of said gas are recirculated in each of the downstream parts of the other two lines in which the entire excess flow per se and the second and third part of the recirculated flow are withdrawn through the corresponding by-pass discharge.

According to a more specific characteristic of the invention, the constant flow is ensured, in each line, by means of a calibrated restriction operating in sonic rate, the pressure upstream of the calibrated restriction being dimensioned to control at least the flow regulator of the associated by-pass discharge.

It is another object of the present invention to propose a device for supplying a gas to an analyzer enabling carrying out the process mentioned above of the type comprising:

a source of gas to be analyzed;
a source of calibration gas;
a first line, including a first flow regulator means, directly connecting the source of gas to be analyzed to a section of the input line of the analyzer;
a second line, connected upstream to the source of gas to be analyzed and including in series a gas purifier and a second flow regulator means; and
at least a third line, including a third flow regulator means, connected to a source of calibration gas initially containing a larger quantity of traces than the gas to be analyzed, and downstream, to a downstream part of the second line,
characterized in that each line includes, in an upstream part, a calibrated restriction defining a sonic throat and, in an intermediate part thereof, a discharge by-pass provided with a discharge flow regulator.

According to another characteristic of the invention, each line comprises, immediately upstream of the restriction in this line, a pressure pick-up which is typically mounted on a pressure measuring by-pass which opens in the atmosphere through a calibrated orifice.

With the process and the device according to the invention, each line is permanently and completely flushed away with a flow of gas, upstream by the gas which circulates in the line and, downstream and in a non-operative step, with a recirculated gas protion originating from another line. In the active portion of each line, there is only one orifice or one calibrated restriction, naturally not very polluting and in the present case treated to be substantially not susceptible to add impurities in view of the permanent flushing of the line. The polluting components such as the pressure pick ups and the flow regulators are mounted in by-passes of the line per se, also permanently flushed with a flow of gas. The calibrated restrictions in the lines operating in sonic rate, the gas flows in the lines downstream of the restrictions are dependent only on the upstream pressure and may therefore be easily calculated from the latter, which enables ensuring an accurate operation, with very little variation in time, and which may be corrected, of the system according to the invention.

BRIEF DESCRIPTION OF DRAWINGS

Other characteristics and advantages of the present invention will appear from the description which follows of embodiments, given by way of illustration but without limitations, with reference to the annexed drawings, in which:

FIG. 2 is a schematic view of another embodiment of a device according to the invention.

DESCRIPTION OF PREFERRED EMBODIMENTS

Figure 1:
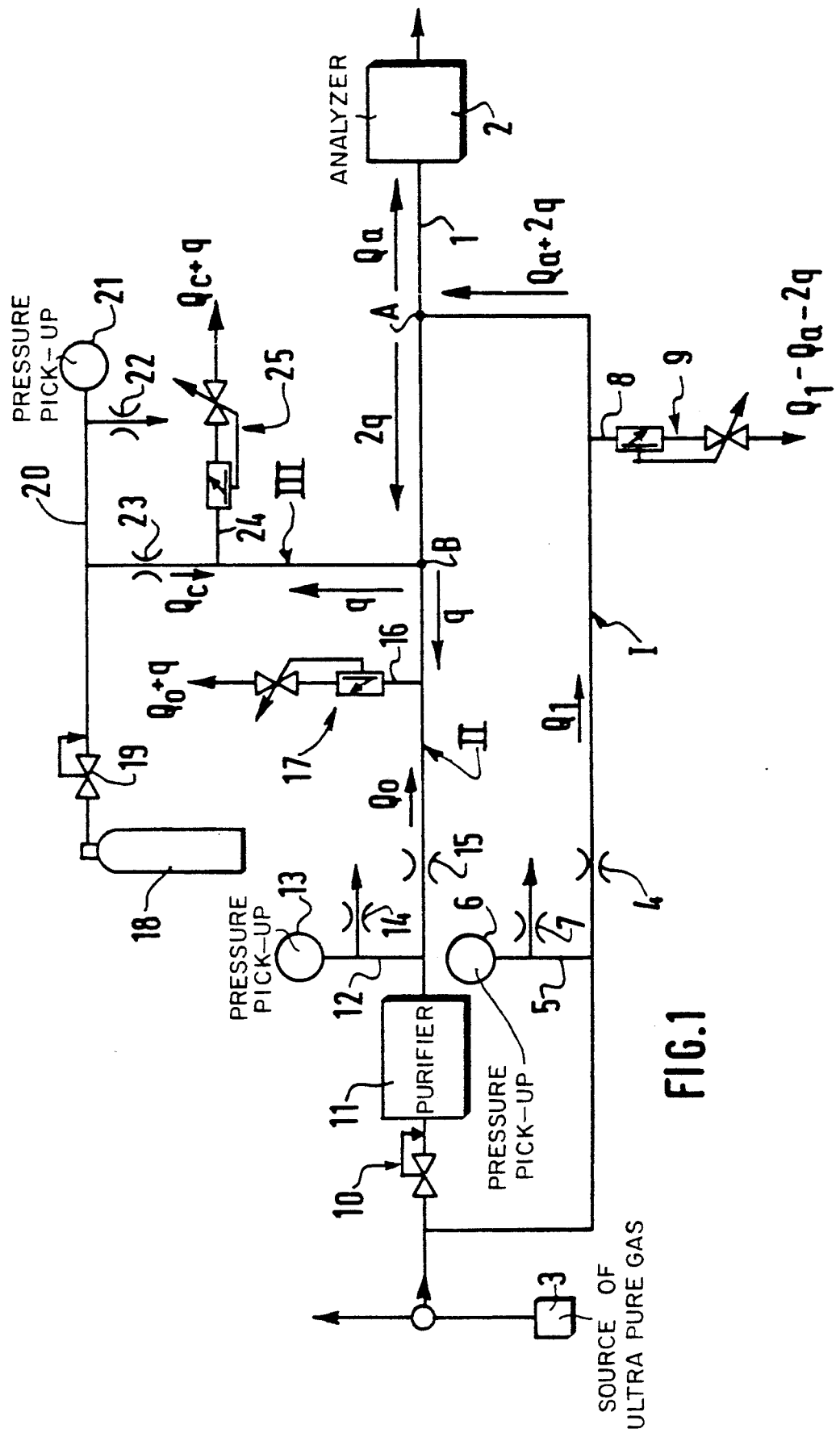
FIG. 1 is a schematic view of the device for carrying out the process of supplying gas according to the invention, the gas flows illustrated corresponding to a step of analysis of the gas to be analyzed.

In the description which follows and on the drawings, identical or analogous items are referred to by the same reference numerals.

The device illustrated in FIG. 1 includes three lines, I, II, III typically killed and polished stainless steel tubes, for selectively supplying gas to a section of an input line 1 to a very high sensitive analyzer 2, adapted to analyze traces of residual gas in a main gas originating from a source of ultra-pure gas 3, typically for the continuous measurement of possible traces in a gas prepared in situ with an equipment for supplying gas 3, for example, a generator of high purity nitrogen (HPN).

The gas originating from source 3 is fed, at a pressure generally comprised between 5 and $15 \times 10^5$ Pa, to a first line I, or line of analysis, and to a line II, both being connected downstream, at A, to the inlet section 1 of the analyzer 2.

Line I has a restriction 4, typically a calibrated orifice, operating in sonic rate and, upstream of the restriction 4, a pressure measuring by-pass 5, provided with a pressure pick-up 6 upstream of a calibrated charge loss 7 providing for a very low escape flow in the by-pass 5. Line I comprises, in the downstream portion, a discharge by-pass 8 provided with a controllable flow regulator 9.

Line II, adapted to supply to the analyzer 2, the "zero" gas and the diluted calibration gas, includes, in the upstream portion, a pressure regulator 10, and in series, purifier 11, for example of the adsorbent type or of the chemical purifying type called "GETTER". Downstream of the purifier 11, line II includes, similarly as is the case for line I, a pressure measuring by-pass 12, with a pressure pick-up 13 and a discharge calibrated orifice 14, a calibration restriction 15 and a discharge by-pass 16 provided with a controllable flow regulator 17.

Line III establishes communication between a storage container for a calibration gas 18, provided with a mano-pressure reducer 19 and containing a gas of the same type as the gas to be analyzed with the same traces but in an amount of the order of 1000 to 10,000 times higher. Line III communicates with line II at a point B located downstream of the by-pass 16 and upstream of point A. Line III, similarly as the other lines, includes, consecutively, a pressure measurement by-pass 20 with a pressure pick-up 21 and a discharge calibrated orifice 22, a calibrated restriction 23 and a discharge by-pass 24 provided with a controllable flow regulator 25.

The operation of the process according to the invention will now be described in connection with the step of gas analysis. The restrictions 4, 15 and 23 determine constant gas flows $Q_1$, $Q_0$, and $Q_C$, respectively in lines I, II and III. In the analysis step, lines II and III are not used, and the gas which comes from source 3 is directly sent, via line I to the analyzer 2. The analyzer 2 operates with a given inlet flow of gas $Q_a$, of the order of 1 liter/minute. The nominal flow $Q_1$, defined by restriction 4 is determined so as to be greatly in excess with respect to the given flow $Q_a$, such as $Q_a + 2_q$, q being a flushing flow arbitrarily selected to be of the order of 0.2 liter/minute. In this analysis step, the regulator 9 in the discharge by-pass 8 of line I is adjusted so as to allow a leaking flow $Q_1 - Q_a - 2_q$ to escape. At point A, the flow $(Q_a + 2_q)$ downstream of line I is divided into a flow $Q_a$ in the input section 1 and a flow $2_q$ in the downstream portion AB of line II. At point B, the recirculation flow $2_q$ is divided into a flow q in line II and a flow q in line III. According to the process of the invention, the flow regulator 17 in the discharge by-pass 16 of line II is adjusted so as to withdraw from line II, the nominal flow $Q_0$ produced by restriction 15 and the above mentioned recirculation flow q. Similarly, flow regulator 25 of line III is adjusted so as to withdraw from this line III all the nominal flow $Q_c$ produced by restriction 23, and the recirculation flow q. As seen, all the active circuit portions of the device according to the invention are simultaneously flushed with a flow of gas according to the object of the invention.

The operation is similar during the other step of supplying gas to the analyzer. Thus, when supplying gas "zero" through line II, regulator 17 of line II by-passes a flow $Q_0 - Q_a - 2_q$, the regulator 25 of line III by-passing the same flow $Q_c + q$ as previously and the regulator 9 of line I by-passing from the latter a flow $Q_1 + q$.

In the embodiment of FIG. 2, the elements of the system of FIG. 1 are found here with more calibration lines including a line III' analogous to line III, previously described, with a source of calibration gas which is different from storage container 18, and line IV for calibrating traces of gas in liquid phase, for example, $H_2O$ starting from a point D of line II between the purifier 11 and the calibration 15 and meeting input section 1 to the analyzer 2 at point C downstream of junction point A of line I. Line IV includes, as is the case of lines I to III, an upstream calibration 26 followed by a first discharge by-pass 27 provided with a flow regulator 28 enabling providing a humidifier 29 with a specific constant flushing flow, then a second discharge by-pass 30 provided with a flow regulator 31. The humidifier 29, for example of the permeator type, is supplied, at 36, with a source of liquid under pressure. The pressure pick-up 13 is common to lines II and IV. As compared to the embodiment of FIG. 1, the input section 1 to the analyzer 2 is extended downstream by means of a first discharge by-pass 32 provided with a check valve 33 and with a second discharge by-pass 34 provided with a flow regulator 35.

To ensure a particularly reliable quality of analysis which is independent of the variations of pressure and temperature of the gas to be analyzed, the device according to the invention may advantageously, as illustrated in FIG. 2, be automated, the pressure pick-ups 6, 13, and 21 continuously supplying to a central control unit 38, typically of the micro-processor type, pressure signals which, as compared to referenced values, are stored in the central unit 38, and enable the latter to send to the various flows regulators 9, 17, 25, 28, 31 and 35, control signals to adjust the opening of the latter to the real flow circulating in the lines and thereby obtaining pressures measured by the pressure detectors.

We claim:

1. Process for supplying a gas to a trace analyzer of very high sensitivity comprising the steps of sequentially supplying to an input line to the analyzer of a given flow:
   a) of a gas to be analyzed, via a first line;
   b) of a pure gas prepared by purifying the gas to be analyzed, via a second line;
   c) of at least one calibration gas, which is diluted with the pure gas, initially containing a greater quantity of traces than the gas to be analyzed, via a third line,
   the downstream parts of the three lines being connected to said input line,
   wherein the gas permanently runs through the upstream parts of each of the three lines at a constant flow, there is provided in an intermediate part of each line a discharge by-pass which is provided with a controllable flow regulator, said constant flow in the first and second lines being higher than said given flow, and the flow regulators are controlled for step a) so that a first part of the gas flow in the first line is discharged through the associated discharge by-pass and second and third parts of the flow in the first line are respectively discharged from the discharge by-passes of the second and third lines in combination with the respective constant flows in the second and third lines, the constant flow in the upstream part of the first line equaling the sum of said given flow and said first and second and third parts of the flow in the first line.

2. Process according to claim 1, wherein the constant flow in each line is ensured by a calibrated restriction operating in sonic rate and wherein the pressure is measured upstream of the calibrated restriction to operate at least the flow regulator of the associated discharge by-pass.

3. Process according to claim 2, wherein the pressure is measured in a pressure measurement by-pass through which a small leaking flow runs permanently.

4. Apparatus for supplying gas to a very highly sensitive trace analyzer, comprising:
   a source of gas to be analyzed;
   a first line, including a first flow regulator means, directly connecting the source of gas to be analyzed to an input line to the analyzer;
   a second line having an upstream end connected to the source of gas to be analyzed and including, in series, a gas purifier and a second flow regulator means; and
   a third line, including a third flow regulator means, connected to a source of calibration gas containing a greater quantity of traces than the gas to be analyzed, and downstream, to a downstream portion of the second line,
   wherein each line includes, in an upstream portion, a calibrated restriction defining a sonic throat and, in an intermediate portion, a discharge by-pass provided with a discharge flow regulator.

5. Apparatus according to claim 4, wherein each line comprises a pressure pick-up immediately upstream of the restriction.

6. Apparatus according to claim 5, wherein the pressure pick-up is mounted on a pressure measurement by-pass opening into the atmosphere through a calibration orifice.

7. Apparatus according to claim 4, wherein the input line communicates, downstream, with a discharge duct provided with a discharge flow regulator.

8. Apparatus according to claim 4, which comprises at least two third lines.

9. Apparatus according to claim 8, wherein at least one third line is connected, upstream, to the second line, between the purifier and the calibrated restriction of this second line, and downstream, to a section of the input line and comprises, upstream of the discharge duct, a generator of traces which is flushed under constant flow.

10. Apparatus according to claim 9, wherein the trace generator introduces into the third line traces from a source of liquid.

* * * * *